(12) United States Patent  (10) Patent No.: US 7,628,960 B2
Ruddock  (45) Date of Patent: Dec. 8, 2009

(54) LIQUID HANDLING ROBOT FOR WELL PLATES

(75) Inventor: Trevor Ruddock, Dorset (GB)

(73) Assignee: Genetix Limited, Hampshire (GB)

( * ) Notice: Subject to any disclaimer, the term of this patent is extended or adjusted under 35 U.S.C. 154(b) by 64 days.

(21) Appl. No.: 11/498,839

(22) Filed: Aug. 4, 2006

(65) Prior Publication Data

US 2006/0269447 A1 Nov. 30, 2006

Related U.S. Application Data

(62) Division of application No. 10/144,763, filed on May 15, 2002, now Pat. No. 7,105,129.

(51) Int. Cl.
*B01L 3/02* (2006.01)
(52) U.S. Cl. .......................... 422/100; 422/63
(58) Field of Classification Search .................. 422/100, 422/63
See application file for complete search history.

(56) References Cited

U.S. PATENT DOCUMENTS

| | | | |
|---|---|---|---|
| 3,650,306 A | | 3/1972 | Lancaster |
| 5,139,744 A | | 8/1992 | Kowalski |
| 5,369,566 A | | 11/1994 | Pfost et al. |
| 5,906,795 A | * | 5/1999 | Nakashima et al. ......... 422/100 |
| 5,948,362 A | | 9/1999 | Steinbrenner et al. |
| 6,079,593 A | | 6/2000 | Konrad |
| 6,116,099 A | | 9/2000 | Carl |
| 6,182,719 B1 | | 2/2001 | Yahiro |
| 6,325,114 B1 | | 12/2001 | Bevirt et al. |
| 6,544,480 B1 | | 4/2003 | Veighe et al. |
| 2001/0046437 A1 | | 11/2001 | Bramwell et al. |
| 2002/0051737 A1 | | 5/2002 | Sollböhmer et al. |

FOREIGN PATENT DOCUMENTS

| | | |
|---|---|---|
| EP | 0 801 309 A2 | 10/1997 |
| EP | 1 275 966 A1 | 1/2003 |
| WO | WO 01/69263 A1 | 9/2001 |

* cited by examiner

*Primary Examiner*—Jill Warden
*Assistant Examiner*—Natalia Levkovich
(74) *Attorney, Agent, or Firm*—Foley & Lardner LLP

(57) ABSTRACT

A liquid handling robot for handling well plates. The robot has a powered anvil which loads pipette tips from a tray onto the cones of a liquid handling head by first clamping the liquid handling head to the anvil and then ramming a movable plate carrying the pipette tips onto the cones. The robot also allows for fully automated swapping between different heads, such as liquid handling heads or pin heads. A head parking station is provided for parking heads when they are not being used. The robot has an automated pipette tip tray dispenser based on storage cassettes that store vertically stacked pipette tip trays. The trays are dispensed one at a time out of the storage cassette past retaining catches which are normally inwardly positioned to carry the pipette tip trays, but are outwardly biasable by a dispensing mechanism to allow the lowest tray in the shaft to pass onto a conveyor which moves the tray to a pick-up position from which the head can move the tray to the powered anvil for pipette tip loading onto a liquid handling head.

13 Claims, 14 Drawing Sheets

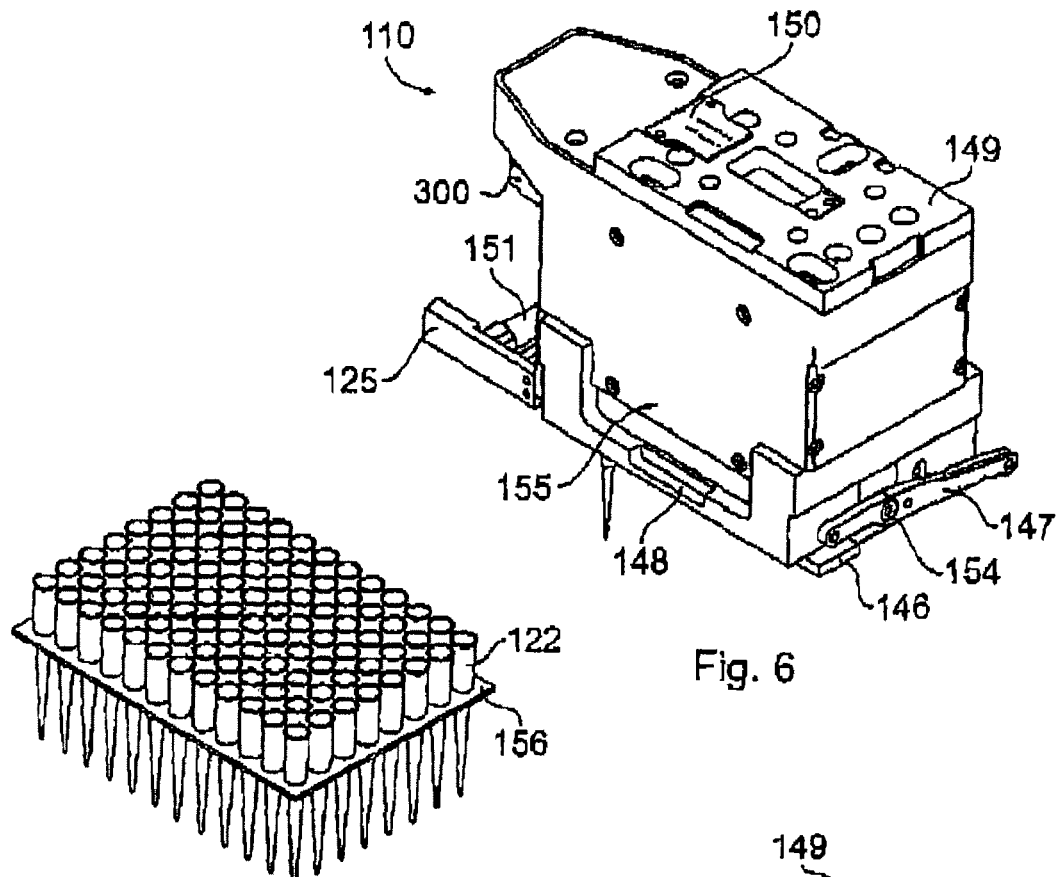
Fig. 6
Fig. 7
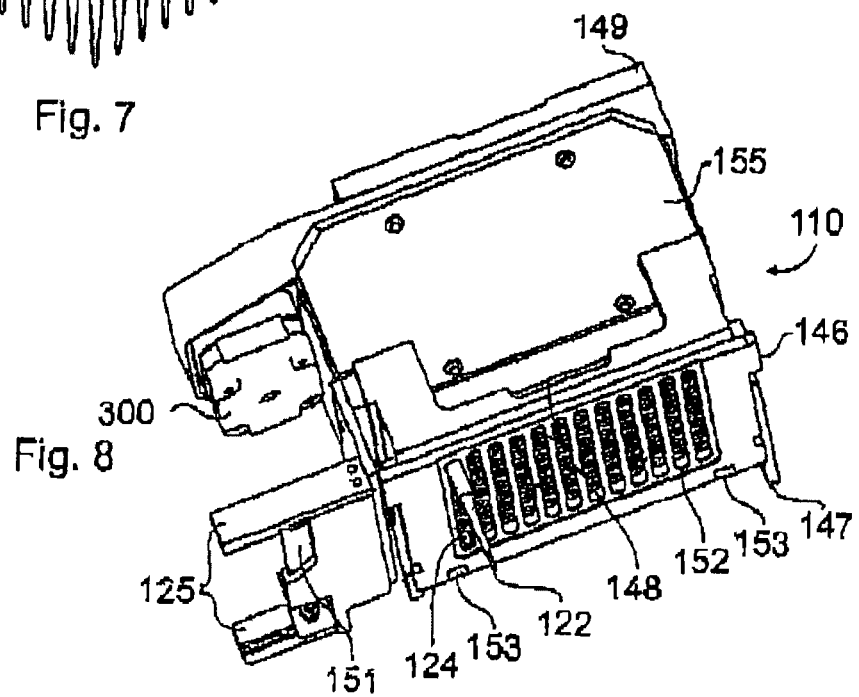
Fig. 8

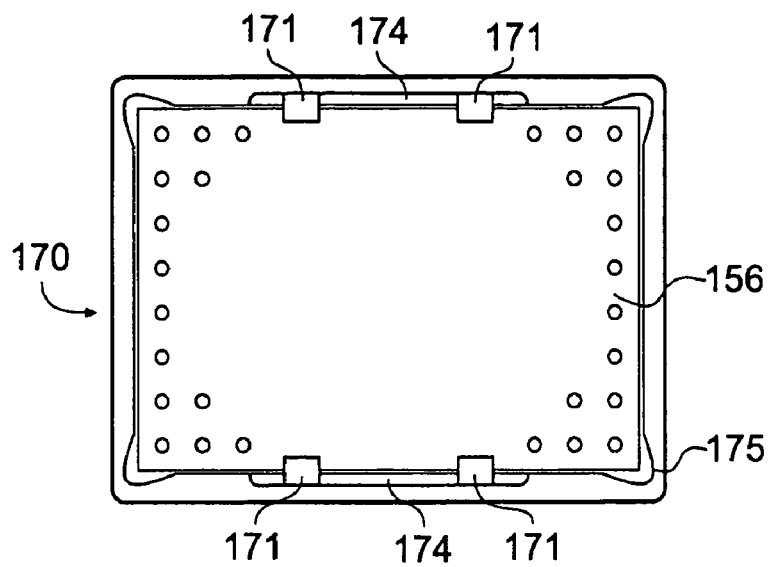
Fig. 14
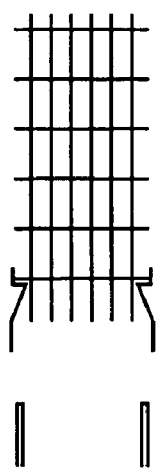 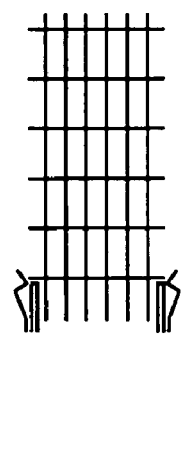 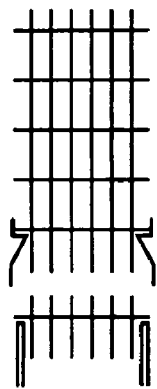 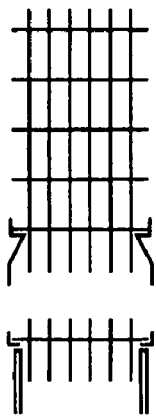
Fig. 15A        Fig. 15B        Fig. 15C        Fig. 15D

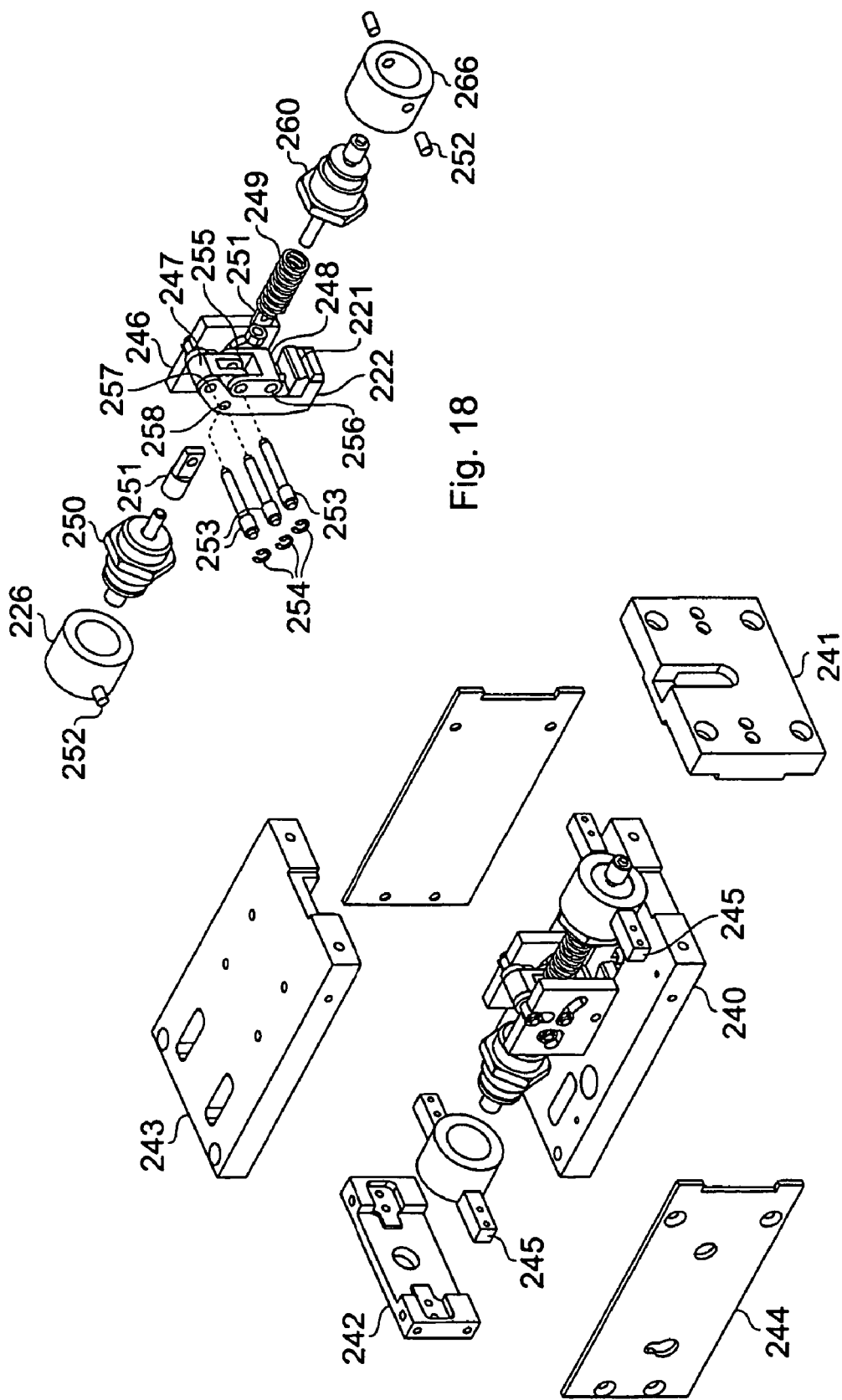

LIQUID HANDLING ROBOT FOR WELL PLATES

CROSS-REFERENCE TO RELATED PATENT APPLICATIONS

This application is a Divisional of U.S. application Ser. No. 10/144,763, filed May 15, 2002, incorporated herein by reference in its entirety.

BACKGROUND OF THE INVENTION

The invention relates to liquid handling robots for well plates which are used in biochemistry and microbiology for processing large numbers of samples in parallel.

FIG. 1 is a perspective view of a liquid handling robot according to the prior art. The robot comprises a movable head 10 that is used for liquid handling and also has a mechanical manipulation capability. The head 10 is movable in three orthogonal axes, x, y and z, with respective motor positioners 12, 14 and 16. Head motion is controlled by a computer control system (not shown) via a control unit 15. The head 10 may also incorporates a camera (not shown) used to perform machine vision functions, such as bar code reading of well plates. The head 10 is movable over a main bed 18 of the apparatus on which well plates and other biological sample containers, such as Q-trays, petri dishes and omni-trays, can be arranged, usually within an experimental area 19. A waste chute 20 is incorporated in the main bed 18 and is flanked by stripping arm posts 21, the purpose of which is described below.

For mechanical manipulation, the head 10 is provided with pincers 25 which are used to grip pipette tip trays. Using the pincers 25 and the positioners 12, 14 and 16, the head 10 can be used to move pipette tip trays around the apparatus as required. The head 10 is also provided with jaws 26 arranged in the horizontal plane for gripping well plates or other sample plates such as omni-trays Q-trays or petri dishes.

FIG. 2 is a perspective view of a pipette tip tray 34 loaded with pipette tips 22. The pipette tips 22 are loaded into trays to allow robotic handling. Each tray is a flat piece of stiff material, such as metal or plastic, with an array of through holes in a grid conforming to the desired well plate standard grid, the through holes having a diameter equal to part of the tapered neck portion of the pipette tips 22, so that pipette tips 22 seat in the through holes.

For liquid handling, the head is provided with an array of pipette tip receiving cones 24 with the array being conformant to the well plate type being processed, for example a 12×8 array for 96-well well plates.

FIG. 3 shows a single pipette tip cone 24 together with an upper end of a pipette tip 22. Each cone 24 has a central capillary leading to a reservoir formed by a barrel and piston, in which the piston is slidable up and down in the barrel to provide a syringing action. The outer surfaces of the cones 24 are corrugated to assist pipette gripping. The cones are made of resilient material to aid formation of a liquid tight seal between themselves and the pipette tips 22 they are designed to receive.

Referring back to FIG. 1, arranged on the main bed 18 of the apparatus there can be seen a pipette tip tray anvil 32. The anvil 32 is a plate with an array of through holes in a grid conforming to one of the well plate standard grids, the through holes having a diameter slightly larger than the outer diameter of the widest part of the pipette tips 22.

A number of trays 34 loaded with unused pipette tips 22 are held in a shelved storage rack 36, sometimes referred to as a "hotel" in the art, with each tray arranged on one shelf and vertically adjacent shelves spaced far enough apart to avoid the pipette tips fouling each other when they are slid in and out of the shelves. In the schematic drawing, the hotel is illustrated as having three racks, each with three shelves. A greater number of shelves would usually be provided in practice.

The action of loading pipette tips 22 onto the liquid handling head 10 is now described. The head 10 is moved over to the pipette tip tray storage rack 36 and, using the pincers 25, one of the pipette tip trays 34 is taken out and placed on the anvil 32. The head 10 is then moved so that the array of cones 24 is aligned above the array of pipette tips 22. Using the lead screw motor drive of the z-positioner 16, the head 10 is then driven down so that the (male) cones 24 mate with the (female) upper apertures of the pipette tips 22, the anvil 32 acting as an abutment surface to allow the pipette tips 22 to be pushed onto the cones 24. The head 10 is then raised away from the anvil 32 using the z-positioner 16 with each of the cones 24 now loaded with a pipette tip 22 ready for liquid handling.

Once the desired pipetting action has been completed, the pipette tips, which are disposable items, can be removed from the head as now described. The head 10 includes a slotted plate (not shown), immediately above the cones 24 with the slots having a width greater than the maximum outer diameter of the cones and less than the maximum outer diameter of the pipette tips 22. The slotted plate is hinged to the main body of the liquid handling head 10. The hinging action allows ejection of pipette tips 22 from the cones 24 on which they are seated. The hinged slotted plate is actuated by a lever acting on the slotted plate being pushed onto the stripping posts 21 as the head 10 is driven down over the waste chute 20. The pipette tips are thus stripped off over the waste chute 20.

Some undesirable aspects of this design have been identified.

The anvil-based pipette tip loading process is not always reliable. The loaded pipette tips can on occasion fall off their cones, especially during syringing out of the liquid reservoir. If this happens, the resultant spillage can destroy the integrity of a whole well plate, which may contain valuable reagents and contain samples obtained from several processing steps already performed.

Manual loading of the pipette tip trays into the shelved storage rack is a fiddly, time consuming exercise, which needs to be performed with care in view of the fact that the pipette tips may be fragile and are held loose in their trays.

The liquid handling robot is not capable of performing other actions, such as gridding or picking, which necessitates transfer of the well plates to another machine if these actions need to be performed before or after the liquid handling actions. Each such transfer, carries a contamination risk, and is also inconvenient.

SUMMARY OF THE INVENTION

Powered Anvil

According to the invention there is provided an anvil apparatus for a liquid handling robot comprising: an apertured plate for receiving an array of pipette tips; a clamping arrangement for holding down a liquid handling head of the liquid handling robot above the apertured plate; and a drive for forcing the apertured plate and the liquid handling head together while the liquid handling head is held down by the clamping arrangement in order to push pipette tips onto the liquid handling head.

The powered anvil of the invention is found to provide enhanced reliability, which is attributed to the fact that a controlled smooth action can be provided for pressing the pipette tips onto the liquid handling head. Moreover, by first clamping the liquid handling head to the anvil, a well defined driving force can be applied with a separate drive so that the driving force can be optimized for the pipette fitting action.

This contrasts with the prior art approach of using the head's own vertical motor drive to force the head down onto the pipette tips. The prior art approach is believed to cause difficulties, since the motor drive of the liquid handling head is principally designed as a positioning device, and is not suited to being used effectively as a ram which may even damage the motor drive and compromise its linearity. The vertical positioner's motor is neither designed to be driven against an immovable object, nor to deliver a controlled reproducible ramming force when it is driven against an immovable object. In particular, it is believed that it is important to apply the force exactly in line with the cones, i.e. perpendicular to the anvil plate surface, for reliable pipette tip loading, and this is not ensured by using the head's vertical positioner drive, since its drive axis is laterally offset from cone array, so a slight hinging, bending or skewing effect may be occurring at the instant of tip loading.

The drive may comprise a jack arranged to push the apertured plate upwards from below. The jack can be implemented with a pneumatically actuated piston assembly. Many other solutions could also be adopted, for example based on motor drives.

The clamping arrangement may comprise movable arms that are actuatable between clamping and free positions to clamp and release the liquid handling head.

The array may conveniently conform to a well plate standard spacing, for example for a well plate having 96 wells or 384 wells. In this regard, it is to be understood that the pipette tip array need not be as large as a whole well plate array. For example, the pipette tip array may be a 4×6 array, covering a quarter of a 96-well well plate which is made up of an 8×12 array of wells.

According to the invention there is further provided a liquid handling robot comprising: an anvil apparatus according to the first aspect of the invention; and a liquid handling head having an array of cones for receiving pipette tips shaped to mate with the clamping arrangement of the anvil apparatus.

Pipette Tip Tray Dispenser

According to the invention there is provided a storage cassette for loaded pipette tip trays comprising: a storage shaft having an internal cross-section shaped and dimensioned to receive vertically stacked pipette tip trays loaded with pipette tips and to allow the pipette tip trays to slide up and down the storage shaft; and a tray retaining mechanism having a retention position in which a lowest one of the pipette tip trays, and thus pipette tip trays vertically stacked above it, are retained in the storage cassette, and a release position in which the pipette tip trays are free to slide down the storage shaft past the tray retaining mechanism.

The tray retaining mechanism may include spring biasing which can be urged into the release position by an actuating force, but otherwise adopts the retention position. Alternatively, a variety of other movable retaining mechanisms could be used. For example, sliding catches drivable by motors between the two positions.

According to the invention there is further provided a pipette tip tray dispenser comprising: a storage cassette according to the invention; and a base unit on which the storage cassette is mountable, the base unit comprising a vertically movable pipette tip tray carrier that can be raised to support the lowest pipette tip tray held in the storage cassette and lowered to carry the lowest pipette tip tray out of the storage shaft beyond the tray retaining mechanism.

The carrier is preferably arranged so that its upward motion to support the lowest pipette tip tray held in the storage cassette moves the tray retaining mechanism from its retention position to its release position and its downward motion allows passage of the lowest pipette tip tray beyond the tray retaining mechanism before the tray retaining mechanism returns to its retention position, thereby allowing the lowest pipette tip tray to be dispensed.

The carrier may advantageously lower the dispensed lowest pipette tip tray onto a conveyor for moving the pipette tip tray away from the storage cassette for subsequent use.

In an embodiment of the invention, the storage cassette is detachably arranged on the base unit.

It is noted that a strength of the pipette tip tray dispenser and storage cassette design is that the dispensing channels and storage cassettes can be used for different pipette tip sizes without any redesign. For example, if two dispensing channels are provided, one can be used with a storage cassette loaded with large volume pipette tips and the other with a storage cassette loaded with small volume pipette tips. A storage cassette loaded with small volume pipette tips installed in one dispensing channel could be swapped with a storage cassette loaded with large volume pipette tips without any reconfiguration of the mechanical components being necessary. The robot control system would however need to be informed.

According to the invention there is further provided a liquid handling robot comprising a pipette tip tray dispenser according to the invention. The liquid handling robot may further comprise a head with a manipulator for removing pipette tip trays from the pipette tip tray dispenser.

Automated Head Attachment

According to the invention there is provided a robot for handling biological sample containers, comprising: a head for carrying out processes on biological sample containers; a positioning apparatus for moving the head around the robot; and a parking station for parking the head, wherein the head is connected to the positioning apparatus by an attachment mechanism drivable between a clamped state, in which the head is secured to the positioning apparatus, and a released state, in which the head can be detached from the positioning apparatus and deposited in the park station.

The park station preferably comprises a plurality of parking bays, each for parking one head. This allows different types of head to be stored ready for action, and also spare heads of the same type in case the head being used suffers a failure.

The robot will typically be provided with multiple heads, for example two or more liquid handling heads, a mixture of liquid handling and pin heads, or two or more pin heads, thereby providing a flexible multi-purpose robot, capable of carrying out a variety of liquid handling, spotting, gridding and colony picking tasks.

In an embodiment of the invention, the attachment mechanism comprises a piston assembly arranged to actuate a knee joint connected to a latch, the knee joint adopting a bent position in the released state and straightened position in the clamped state. The piston assembly may advantageously include two piston cylinder units arranged in a push-me-pull-you configuration either side of the knee joint.

The attachment mechanism may include a communication feed-through, and each head resident logic that allows the robot through the communication feed-through to receive identification data from any head that is attached to the positioning apparatus.

Liquid Handling Robot Combining at Least Two of the Powered Anvil, Pipette Tip Tray Dispenser and Automated Head Attachment It will be understood that the powered anvil, pipette tip tray dispenser and automated head attachment can be advantageously combined in a single liquid handling robot. In particular the combination of automated pipette tip tray dispenser and powered anvil is a powerful combination which allows for rapid and reliable liquid handling of well plates using disposable pipette tips. Liquid handling is further enhanced by the ability to swap between multiple liquid handling heads in a fully automated fashion, the heads being specialized to perform different tasks. For example, different liquid handling heads may be provided for large and small volume pipette tips, and the pipette tip tray dispenser can be loaded with two storage cassettes, one carrying large volume pipette tips and the other low volume pipette tips which are then independently dispensable through separate dispensing channels. In addition, the ability to be able to integrate picking or gridding functions within the liquid handling processes that is made possible by the automated head swapping capability opens up a whole range of new applications possibilities which would hitherto have necessitated using different robots and moving samples manually between them.

The various possible combinations of any two of the powered anvil, pipette tip tray dispenser and automated head attachment, or the combination of all three, thus provide new and powerful functionalities additional to the independent functionalities of each item.

BRIEF DESCRIPTION OF THE DRAWINGS

For a better understanding of the invention and to show how the same may be carried into effect reference is now made by way of example to the accompanying drawings in which:

FIG. 6 is a perspective view of a liquid handling head for pipetting up to 250 ml per pipette;

FIG. 7 is a perspective view of a pipette tip tray loaded with pipette tips;

FIG. 8 is a further perspective view of the liquid handling head from a different perspective than FIG. 6 showing the underside of the liquid handling head;

FIG. 14 is a view from below of a storage cassette loaded with pipette tip trays;

FIGS. 15A-D are schematic end views showing four steps in dispensing a pipette tip tray from a storage cassette;

FIG. 18 is an exploded perspective view of the head latching mechanism of the head latching unit;

FIG. 19 is an exploded perspective view of the head latching unit with the head latching mechanism of FIG. 18 partly assembled;

DETAILED DESCRIPTION

Machine Overview

Figure 4:
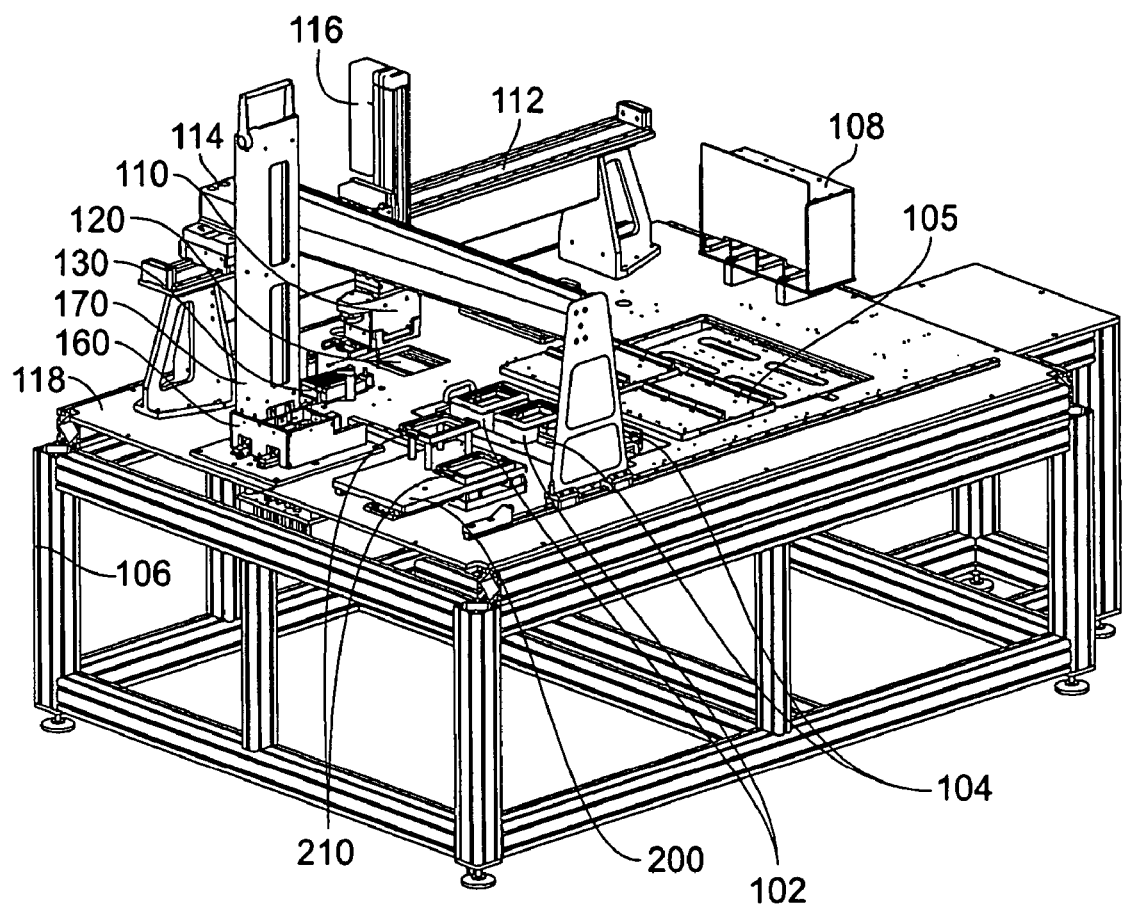
FIG. 4 is a perspective view of a liquid handling robot according to an embodiment of the invention comprising an automated pipette tip tray dispenser, powered anvil, and automated head swapping components.

FIG. 4 is a perspective view of a liquid handling robot according to an embodiment of the invention. The robot comprises a movable head 110 that is used for liquid handling and also has a mechanical manipulation capability. The head 110 is movable in three orthogonal axes, x, y and z, with respective motor positioners 112, 114 and 116. Head motion is controlled by a computer control system (not shown). The head 110 may also incorporates a camera (not shown) used to perform machine vision functions, such as bar code reading of well plates. The head 110 is movable over a main bed 118 of the apparatus on which well plates and other biological sample containers, such as Q-trays, petri dishes and omnitrays, can be arranged as well as other items such as vacuum manifolds 102 and shakers 104 for processing well plates. Adjacent to the vacuum manifolds 102 and shakers 104 there is a general processing area 105 where well plates, liquid reservoirs and other containers can be arranged for conducting experiments. The main bed of the apparatus is supported at a convenient height on a table frame 106. A waste chute 120 is incorporated in the main bed 118 and is flanked by stripping arm posts (not visible). Situated on the far side of the main bed 118 there is a well plate storage rack 108 with four shelf stacks arranged side by side. A slidable cover for the well plate storage rack is also illustrated. Well plates can be taken out of the storage rack 108 by the head 110 using gripping jaws (not visible).

The robot has a powered pipette tip tray anvil 130 which is described in detail further below with reference to FIGS. 5 to 8.

The robot also has an automated pipette tip tray dispenser 160 which is designed to accommodate two pipette tip tray storage cassettes 170, one for large volume pipette tips (for pipetting up to 250 microliter) and one for small volume pipette tips (for pipetting up to 50 microliter). Only one fitted storage cassette 170 is illustrated. The storage cassettes 170 can be installed and removed from the dispenser 160 by hand. The automated pipette tip tray dispenser 160 and the storage cassettes 170 are described in detail further below with reference to FIGS. 9 to 16.

The robot has the capability of automatically changing between different heads. The available heads for the particular robot configuration can be parked in bays 210 within a park station 200. Two parking bays 210 are shown in the illustrated park station 200. These are for two different liquid handling heads, a large volume item (up to 250 microliters per pipette) and a small volume item (1-50 microliters per pipette). In other embodiments, three, four or more bays could be provided. As well as liquid handling heads, pin heads for colony picking or spotting or gridding could be provided depending on the robot configuration that is desired. The head swapping functionality and associated equipment is described in detail further below with reference to FIGS. 17 to 19.

Powered Anvil

Figure 5:
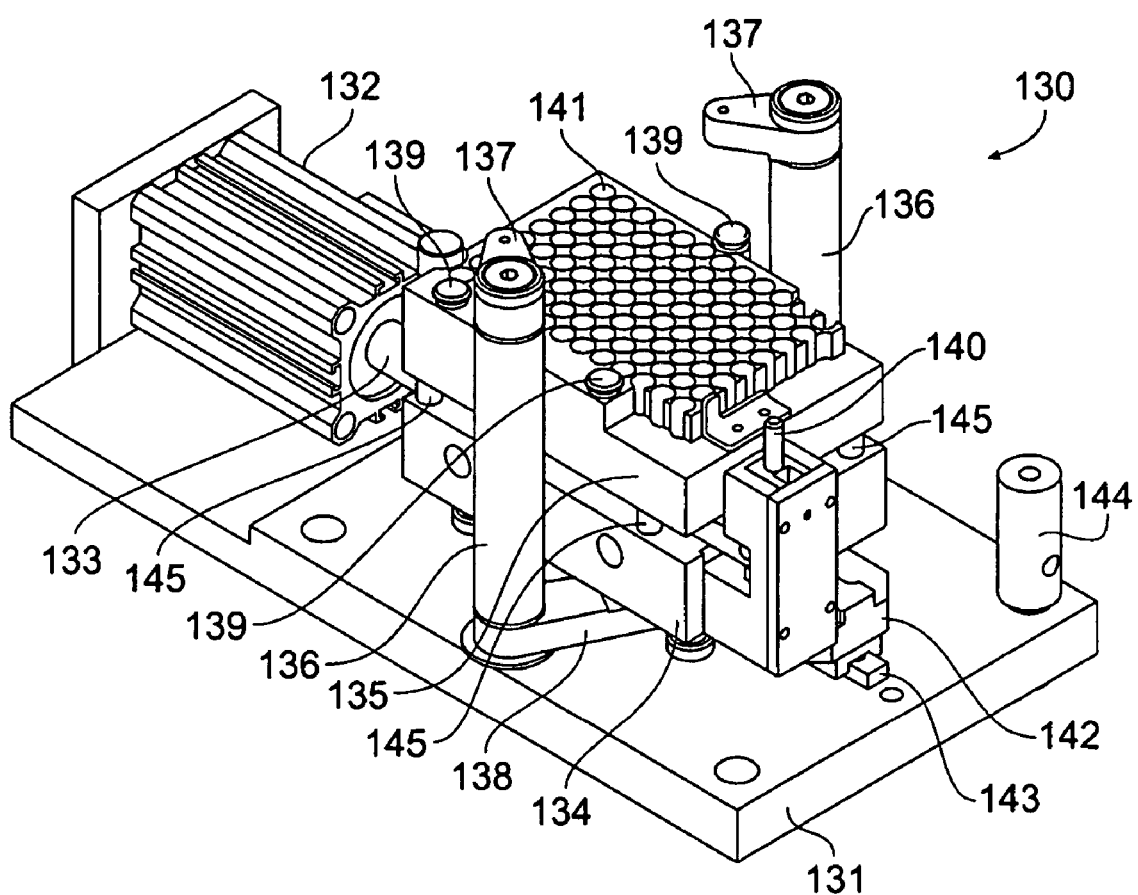
FIG. 5 is a perspective view of the powered anvil.

FIG. 5 is a perspective view of the powered anvil 130. The components of the anvil 130 are arranged on a mounting plate 131 which is bolted to the underside of the main bed of the robot via mounting pillars 144, one of which is shown. The anvil 130 comprises a top plate 135 which is perforated with an array of holes 141 having diameters large enough to loosely receive pipette tips and arranged in a standard well plate grid so as to receive pipette tips loaded into a pipette tip tray. Around the margin of the top plate, three tray clamps 139 are provided. These move apart to a released position when a spigot 140, arranged to one side of the top plate 135 and extending above the plane of the top plate surface, is pushed down. A spring loaded mechanism connects the spigot 140 to the tray clamps 139. In use, a pipette tip tray is loaded into the anvil by lowering the liquid handling head, with a tray gripped in its pincers, down onto the top plate 135, where the head itself depresses the spigot 140 opening up the tray clamps 139 for acceptance of the tray. The head is then raised allowing the spigot 140 to rise with it and thus the tray clamps 139 to move back inwards relative to the top plate 135, thereby clamping the tray in place.

The top plate 135 is arranged spaced apart above a base plate 134, the two being slidably connected by vertically arranged posts 145, wherein the top plate 135 can be slid up and down the posts 145. Movement of the top plate 135 is driven by a pneumatic piston assembly comprising a cylinder unit 132 and piston 133. The cylinder unit 132 is double acting driven by two compressed air feed lines (not shown) and has two stable positions, extended (as illustrated) and retracted. Actuation of the piston 135 moves an elongate cam 142 along a rail 143. The cam 142 has a ramp (not visible) which engages with the underside of the top plate 135 to push it vertically upwards on the posts 145 when the piston 133 moves over a portion of its travel close to its extended position. Motion of the cam 142 also drives rotation of a pair of flippers 137 which act as clamping arms for a robot head. The flippers 137 are mounted on columns 136 that are rotatably mounted in the mounting plate 131. At their lower ends, the columns 136 are connected to inwardly directed lever arms 138 that are in engagement with a waisted portion of the elongate cam 142. Motion of the elongate cam 142 along a portion of the piston's travel, that is closer to the retracted position than the first-mentioned portion of travel, engages one end of the cam's waisted portion with the lever arms 138 to move the latter, thereby rotating the columns 136 and moving the flippers 137.

It will thus be understood that motion of the piston from its retracted position to its extended position initially causes the flippers 137 to move around from an alignment generally parallel to the piston motion direction, to an inwardly pointing alignment as illustrated in FIG. 5, and subsequently causes the top plate 135 to be driven upwards. The significance of these movements is be discussed further below.

Finally in respect of FIG. 5, it is noted that the anvil apparatus 130 is arranged in the robot as illustrated in FIG. 4, with the piston assembly 132, 133 and base plate 134 below the level of the main bed surface. As already mentioned, this is achieved by bolting the anvil apparatus to the underside of the main bed of the robot via the mounting pillars 144.

FIGS. 6 and 8 are perspective views from different angles of a liquid handling head 110 for pipetting up to 250 ml per pipette. The head 110 includes clamping slots 148 arranged to receive the flippers 137 when the head is lowered onto the anvil with a loaded pipette tip tray already in the anvil, and when the flippers 137 are then rotated into the position illustrated in FIG. 5 by motion of the cam. In use, fitting pipette tips onto the head proceeds as follows.

1. A pipette tip tray loaded with pipette tips is placed onto the anvil top plate 135 in the manner described further above.

2. The head is lowered down onto the anvil top plate 135 with the cones 124 aligned with the pipette tips 122 and loosely fitted therein.

3. The piston assembly 132, 133 is actuated with compressed air to drive the piston 133 from its retracted position to its extended position which first rotates the flippers 137 into the clamping slots 148 to hold down the head, and second jacks the anvil top plate 135 upwards to ram the upper ends of the pipette tips 122 into the 124 cones.

Here it will be understood that the clamping action of the flippers 137 serves to provide an abutment preventing upward motion of the head 110 in response to the upward driving force of the top plate 135 imparted by the ramped cam 142. In this way, the pipette tips 122 can be fitted to the cones 124 with a controlled force acting in a controlled direction, which provides for highly reliable liquid tight pipette tip attachment to the cones.

Other parts of the head 110 are now described.

The head 110 is provided with pincers 125 which are used to grip pipette tip trays. The pincers 125 are driven by a motor drive 151. Using the pincers 125 and the robot's x-, y- and z-positioners, the head 110 can be used to move pipette tip trays around the apparatus as required. The head 110 is also provided with jaws (not shown) for gripping well plates or other sample plates such as omni-trays Q-trays or petri dishes. The jaws are arranged on the opposite side of the head 110 to the pincers 125.

The head 110 is provided with an array of pipette tip receiving cones 124, one of which is illustrated in FIG. 8. The cones 124 are arranged in an array that is conformant to the well plate type being processed, which in this example is a 12×8 array for 96-well well plates. A single pipette tip 122 is also shown in FIG. 8 for illustration purposes.

Figure 3:
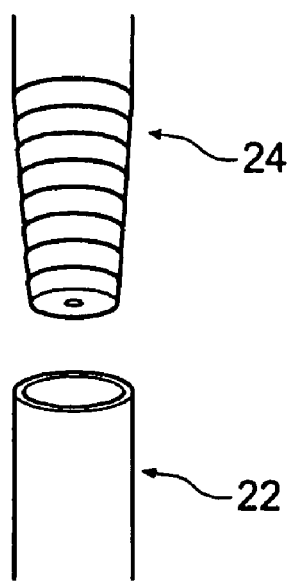
FIG. 3 shows a pipette tip cone and upper end of a pipette tip.

Each cone 124 is as illustrated in FIG. 3 with a central capillary leading to a reservoir formed by a barrel and piston, in which the piston is slidable up and down in the barrel to provide a syringing action. The reservoirs are located in the interior of the main body 155 of the head 110. The outer surfaces of the cones 124 are corrugated to assist pipette gripping. The cones 124 are made of resilient material to aid formation of a liquid tight seal between themselves and the pipette tips 122. The head 110 is secured to the z-positioner via a securing plate 149 on its upper side. The securing plate 149 also provides a host for an electrical contact pad 150 which mates with a corresponding contact pad on the z-positioner. The contact pad 150 provides the head 110 with electrical power feeds for driving the pincer motors, syringing pistons and other functions and also communication feedthroughs for providing communication lines from the main robot to the resident logic 300 within the head. For example each head has a unique identifier so that the robot can interrogate the head to receive identification data and thus determine the head's identity, which will not only define the head's handling while installed, but also define its parking bay when the heads need to be exchanged or parked.

The bottom side of the head 110 has a slotted plate 146 mounted by hinges 153, with the slots 152 being evident in FIG. 8. The slot width is greater than the maximum outer diameter of the cones 124, but less than the maximum outer diameter of the pipette tips 122. Pipette tips 122 can be stripped from the cones 124, and thus the head 110, by hinging the slotted plate 146. The slotted plate 146 is actuated by a stripping arm 147 which is mounted on a pivot 154 and has one end that protrudes beyond the side of the main body of the head and another end that is situated above an edge flange of the slotted plate 146. In use, the protruding end of the stripping arm is actuated when the head 110 is moved down over the waste chute 120 and encounters a stripping post, which pivots the stripping arm so that its other end pushes down on the flange of the slotted plate 146 causing hinging of the slotted plate. The pipette tips 22 are thus stripped off over the waste chute 120.

Figure 1:
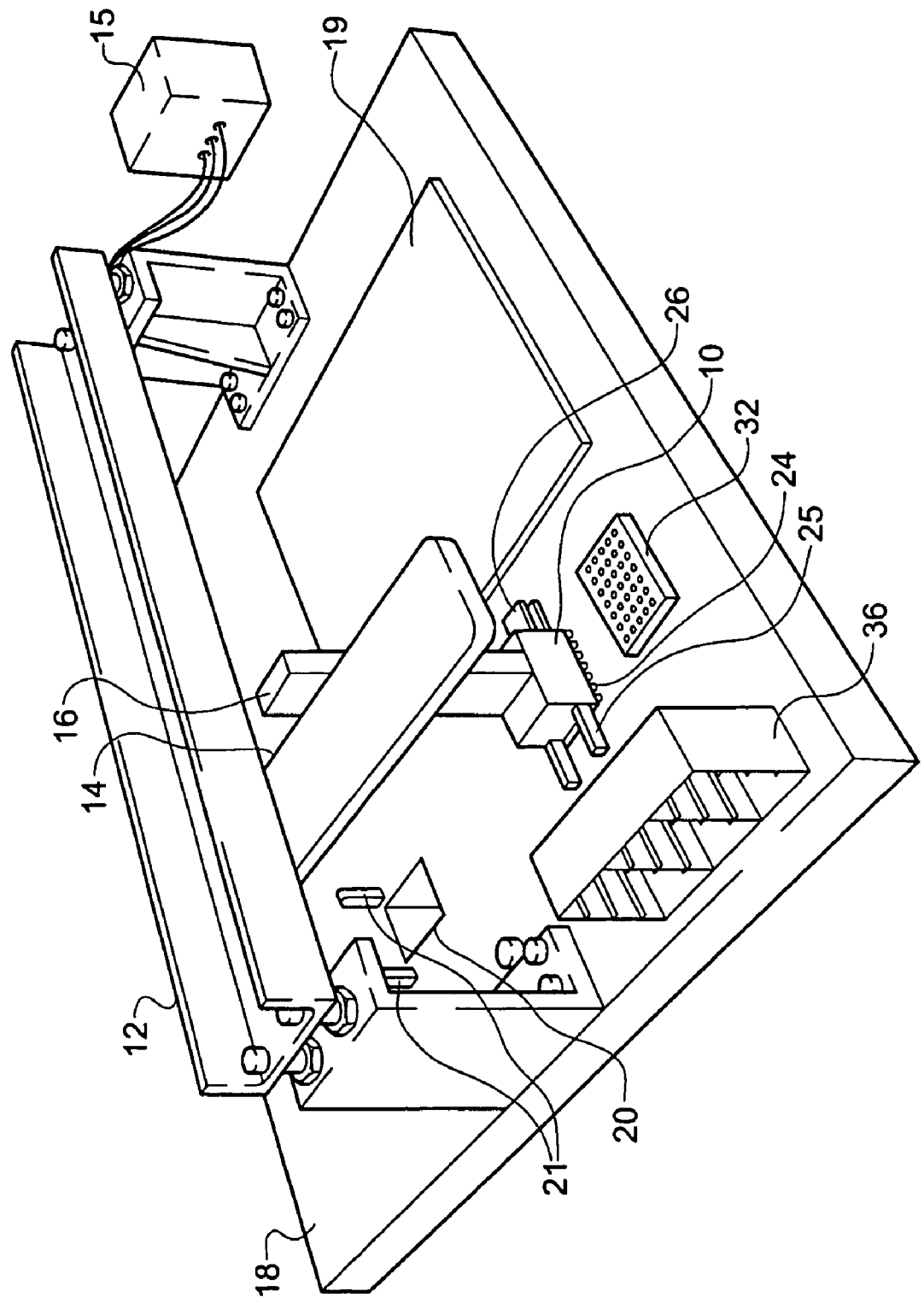
FIG. 1 is a perspective view of a liquid handling robot according to the prior art.
Figure 2:
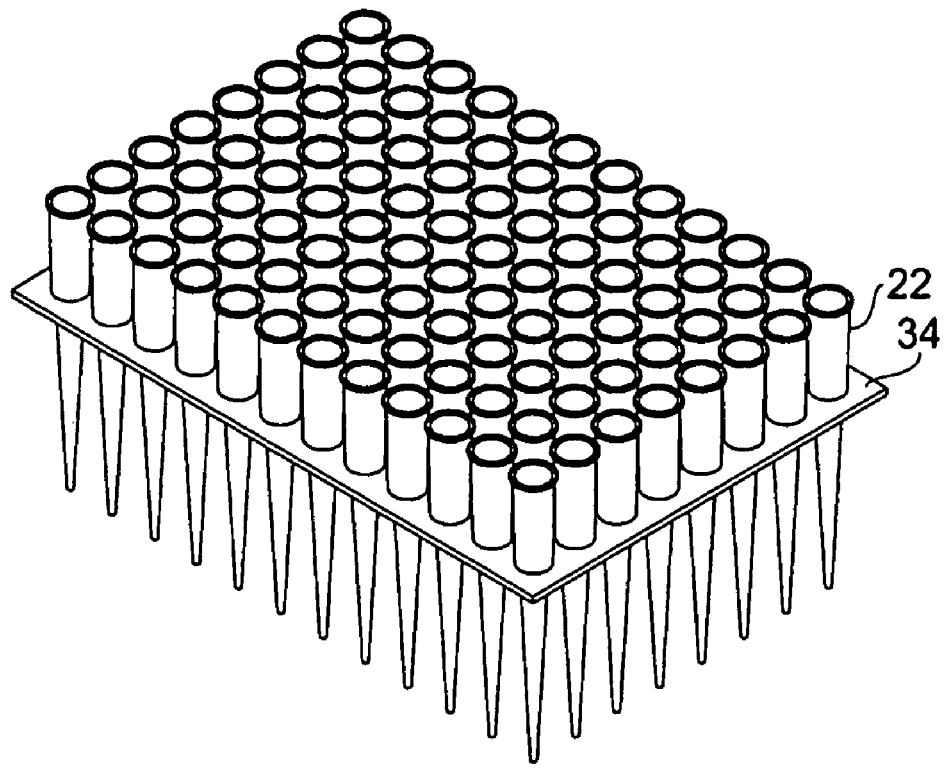
FIG. 2 shows a pipette tip tray loaded with pipette tips.

FIG. 7 is a perspective view of a pipette tip tray 156 loaded with pipette tips 122. (FIG. 7 is the same as FIG. 2, but is reproduced to illustrate a pipette tip tray juxtaposed with a liquid handling head embodying the invention.) The pipette tips 122 are loaded into trays to allow robotic handling. Each tray is a flat piece of stiff material, such as metal or plastic, with an array of through holes in a grid conforming to the desired well plate standard grid, the through holes having a diameter equal to part of the tapered neck portion of the pipette tips 122, so that pipette tips 122 seat in the through holes.

Pipette Tip Tray Dispenser

FIGS. 9 to 12 show views of the pipette tip tray dispenser 160 in perspective, from the end, from the side and from above respectively.

Figure 13:
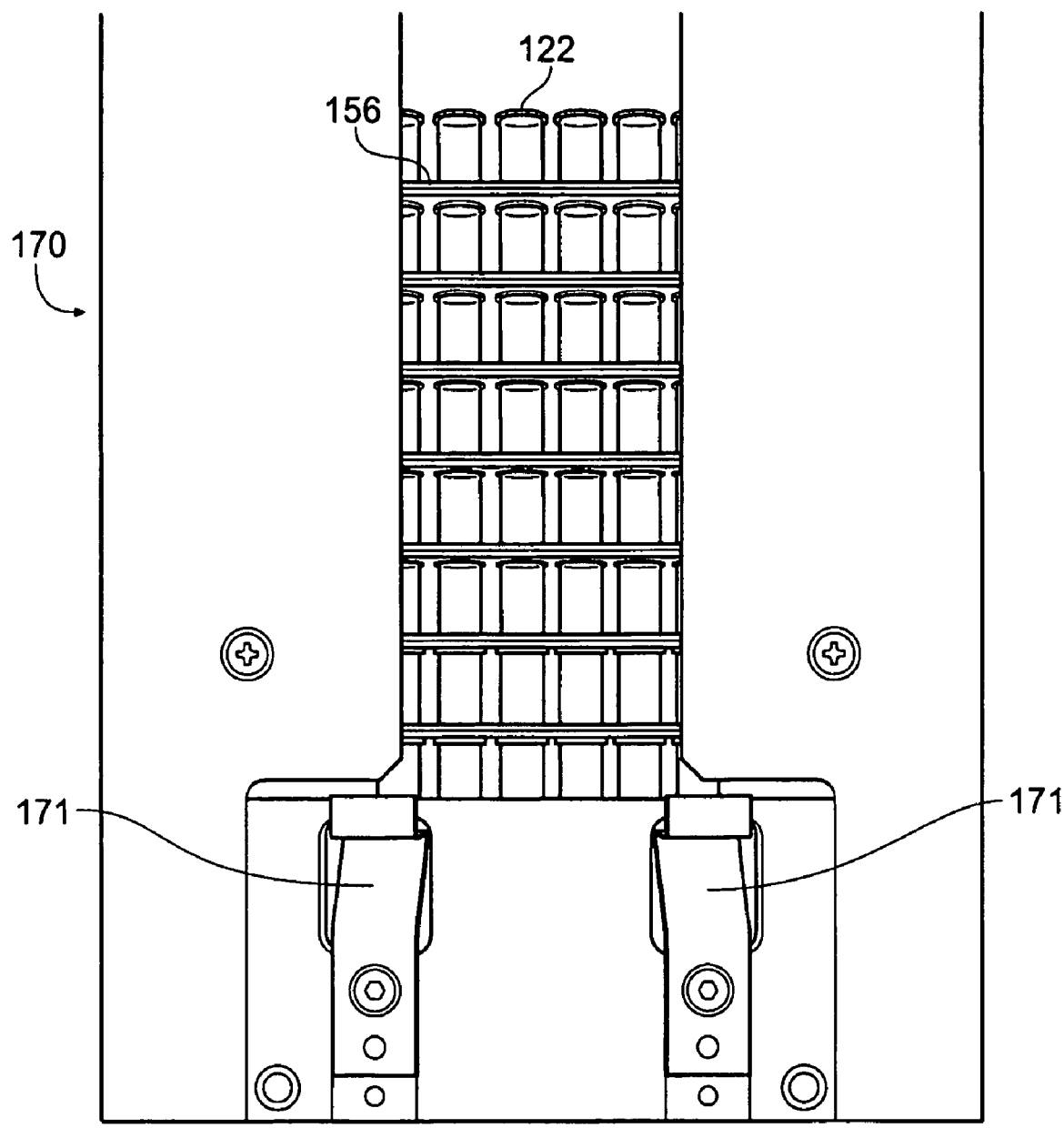
FIG. 13 is a close-up side view of a storage cassette loaded with pipette tip trays.

FIG. 13 is a detail side view of the lower end of a storage cassette 170 loaded with a stack of pipette tip trays 156 loaded with pipette tips 122.

FIG. 14 is a view from below of a storage cassette 170.

The pipette tip tray dispenser 160 is designed to accommodate two pipette tip tray storage cassettes 170, one for large volume pipette tips (for pipetting up to 250 microliter) and one for small volume pipette tips (for pipetting up to 50 microliter). Only one storage cassette 170 is illustrated in order to reveal details of the other storage cassette docking area. The top level of loaded pipette tips 122 carried on a tray 156 within the cassette is also shown.

Each storage cassette 170 is provided with a carrying handle 173 for ease of installation into and removal from the dispenser 160. The storage cassettes 170 stand sleeved in the upper part of the dispenser 160 without locking or latching. The interior of each storage cassette 170 forms a storage shaft 172 having an internal cross-section shaped and dimensioned to receive vertically stacked pipette tip trays loaded with pipette tips. The vertical stacking is such that each pipette tip tray above the lowest one is supported by the upper ends, i.e. the top rim surface, of the pipette tips loaded into the pipette tip tray immediately below. In this stacking position, the lower ends of the pipette tips from each tray (apart from the lowest one) extend into the upper apertures of the pipette tips carried by the tray immediately below. The storage shaft 172 is smooth in the vertical direction to allow the pipette tip trays to slide up and down. The lowest stacked pipette tip tray, and thus any other pipette tip trays stacked vertically above it, are retained in the storage shaft 172 by two pairs of mutually facing spring catches 171 which normally adopt a tray retention position, but can be forced outwards to a tray release position in which pipette tip trays are able to slide down the storage shaft past the catches 171. Tray dispensing is described in more detail further below, after a fuller description of the dispenser 160 has been given.

The dispenser components are mounted to a main plate 161 which bolts to the top surface of the robot main bed 118. A housing 188 formed of two end plates, two side plates and a dividing plate between the side plates is arranged on the upper side of the main plate 161 and defines two generally rectangular apertures for receiving the storage cassettes 170 from above. Two tray dispensing channels are formed by the side plates and dividing plate which are spaced apart by slightly less than the tray width. Trays can be slid along the dispensing channels located in mutually facing L-section ledges 186 machined into the upper, inwardly facing corners of the side and dividing plates. A tray located in the ledges 186 is visible in the left-hand dispensing channel of FIG. 12. Trays are driven along the dispensing channels away from the storage cassette docking area by a conveyor arrangement comprising a fixed base 184 and linearly movable slider 185 which has a dog 187 standing up near the rear end of the slider high enough to push a tray along the dispensing channel that is seated in the L-section ledges. When the slider 185 is fully retracted (as in FIG. 9 for example), the dog 187 is positioned sufficiently close to the rear end of the slider so that it does not foul a tray being dispensed from the storage cassette 170.

Figure 9:
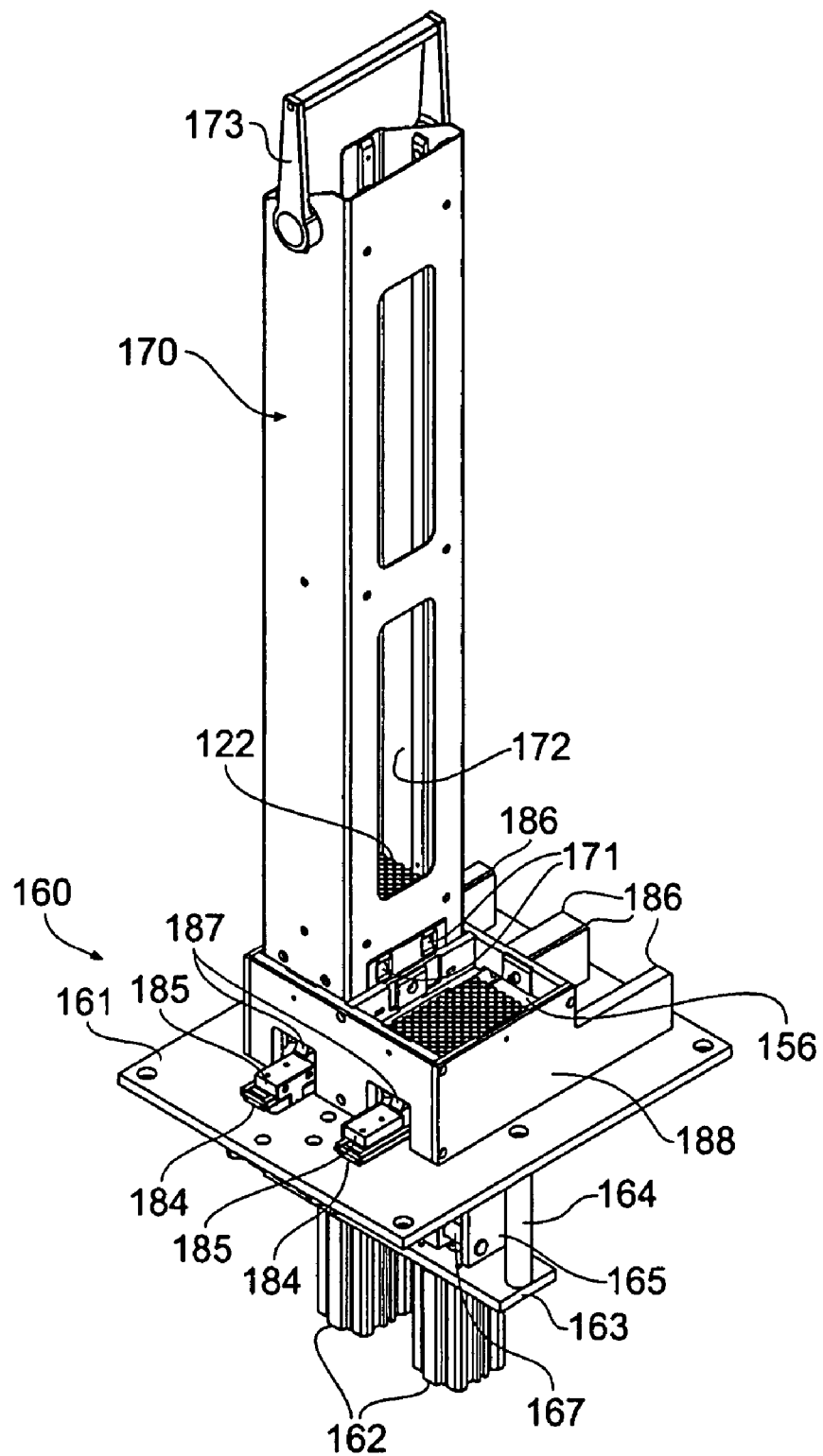
FIG. 9 is a perspective view of the pipette tip tray dispenser.
Figure 10:
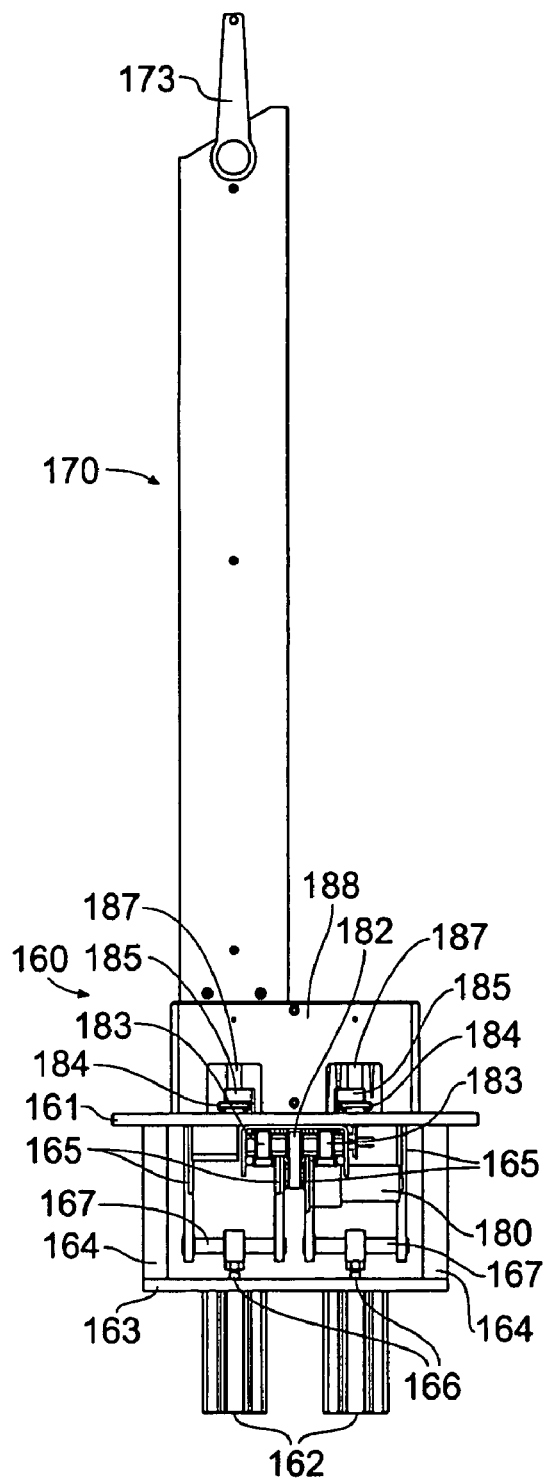
FIG. 10 is an end view of the pipette tip tray dispenser.
Figure 11:
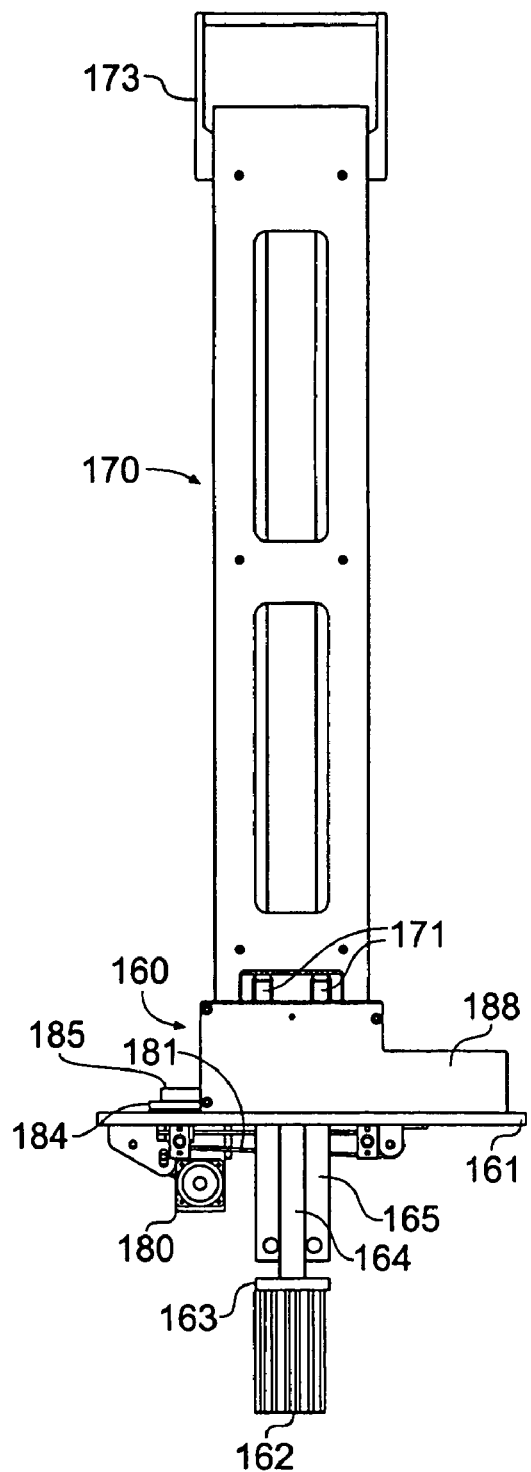
FIG. 11 is a side view of the pipette tip tray dispenser.
Figure 12:
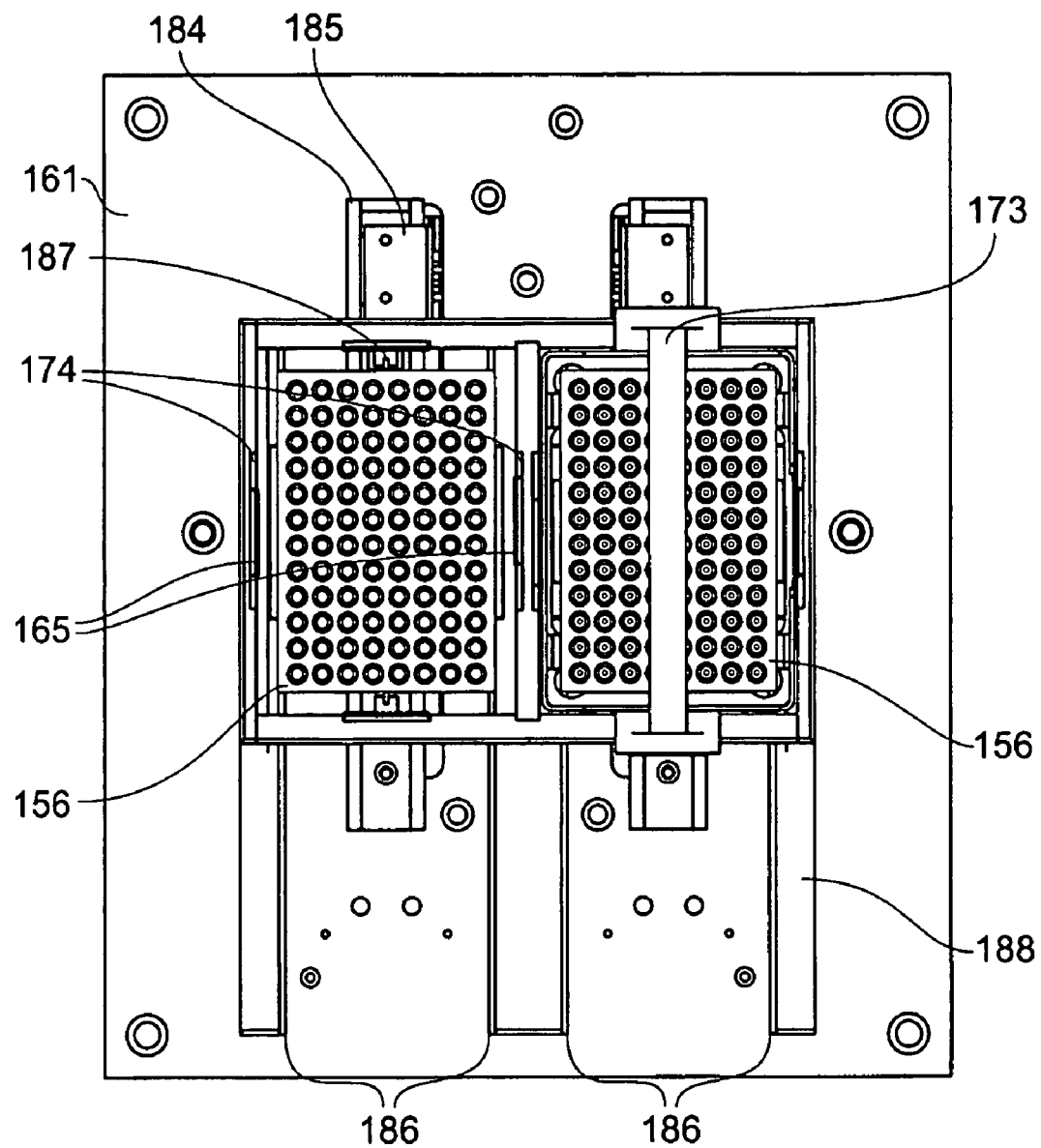
FIG. 12 is a plan view of the pipette tip tray dispenser.

The conveyor drive components are obscured in the perspective view from above of FIG. 9, since they lie below the main plate 161, but are visible in the end and side views of FIGS. 10 and 11. The two sliders 185 can be moved back and forth in unison by a belt drive comprising two belts 181 which are driven from a common electric motor 180 through a succession of toothed gear wheels 182, 183. (If desired, independent conveyor drives could be provided.) Considering one dispensing channel, driving the belt drive in one direction (clockwise in FIG. 11) will cause the dog 187 to push a tray out of the storage cassette docking area to the head pick-up area (tray movement to the right in FIG. 11). Once the dog 187 has reached its end position, the drive direction is reversed (to counterclockwise in FIG. 11), and the dog 187 moves back to the position shown in FIG. 9 ready for pushing another tray along the dispensing channel.

Also arranged on the underside of the main plate 161 are components for driving two pairs of sliding blades 165 that actuate the spring catches 171 of storage cassettes 170 sleeved in the housing 188. The sliding blades 165 are most clearly seen in FIGS. 10, 11 and 12. The sliding blade pairs 165 are spaced apart by a distance slightly less than the tray width. The interior of the lower ends of the storage cassettes is provided with side recesses 174 which allow space for the blades 165 to be moved up into the lower end of the storage cassette sufficiently high to outwardly displace the spring catches 171 and abut the lowest tray held in the storage cassette 170. The side recesses 174 into which the blades can be moved are most clearly evident in FIG. 14 which is a view from below of a storage cassette 170. FIG. 14 also shows corner recesses 175 in the inside of the cassette which are provided to avoid tray jamming.

The actuation mechanism for raising and lowering the blade pairs 165 is now described. The blades of each pair are rigidly connected to each other by a rod 167. Each rod 167 is connected to a piston 166 arranged in a cylinder 162. The piston and cylinder pairs form pneumatic piston assemblies that are driven by compressed air lines (not shown) between an extended (upper) position and a retracted (lower) position. In the retracted position (the one illustrated), the upper edges of the blades 165 lie slightly below the level of the horizontal part of the L-section ledges 186. In the extended position, the upper edges of the blades 165 lie slightly above the level of the lower surface of a tray 156 supported on the spring catches 171. The pneumatic cylinders 162 are bolted hanging down from a cylinder mounting plate 163 which is in turn suspended below the main plate 161 by pillars 164.

FIGS. 15A-D are highly schematic end views showing four steps in dispensing a pipette tip tray from the storage cassette. These are schematic versions of the same view as FIG. 10. To highlight the principles of operation, only the spring catches are shown together with a number of vertically stacked trays filled with pipette tips and a blade pair.

FIG. 15A shows the starting position with a number of filled trays (six in the figure) loaded in the storage cassette, the lowest tray resting on the horizontal surfaces of the spring catches which thereby support the tray stack. The blade pair is in its lowest position with its driving piston retracted.

FIG. 15B shows a subsequent position in which the blade pair has been slid to its uppermost position, with the driving piston extended. In this position, the blades have laterally displaced the spring catches so as to be in contact with the edges of the lowest tray and thereby support the tray stack.

FIG. 15C shows a subsequent position in which the blade pair has been partially withdrawn taking the lowest tray with it. As the blade pair lowers from the uppermost position as shown in FIG. 15B, the spring catches move back into position, but only after the lowest tray has moved past them, thereby catching the next tray as illustrated and thus supporting the remainder of the tray stack.

FIG. 15D shows a subsequent position in which the blade pair is in its lowest position with its upper edges no longer in contact with the dispensed tray which is now resting in the dispensing channel on the L-shaped ledges which are schematically indicated ready for dispensing via the conveyor. After dispensing the tray, the apparatus has returned to the state of FIG. 15A.

Figure 16:
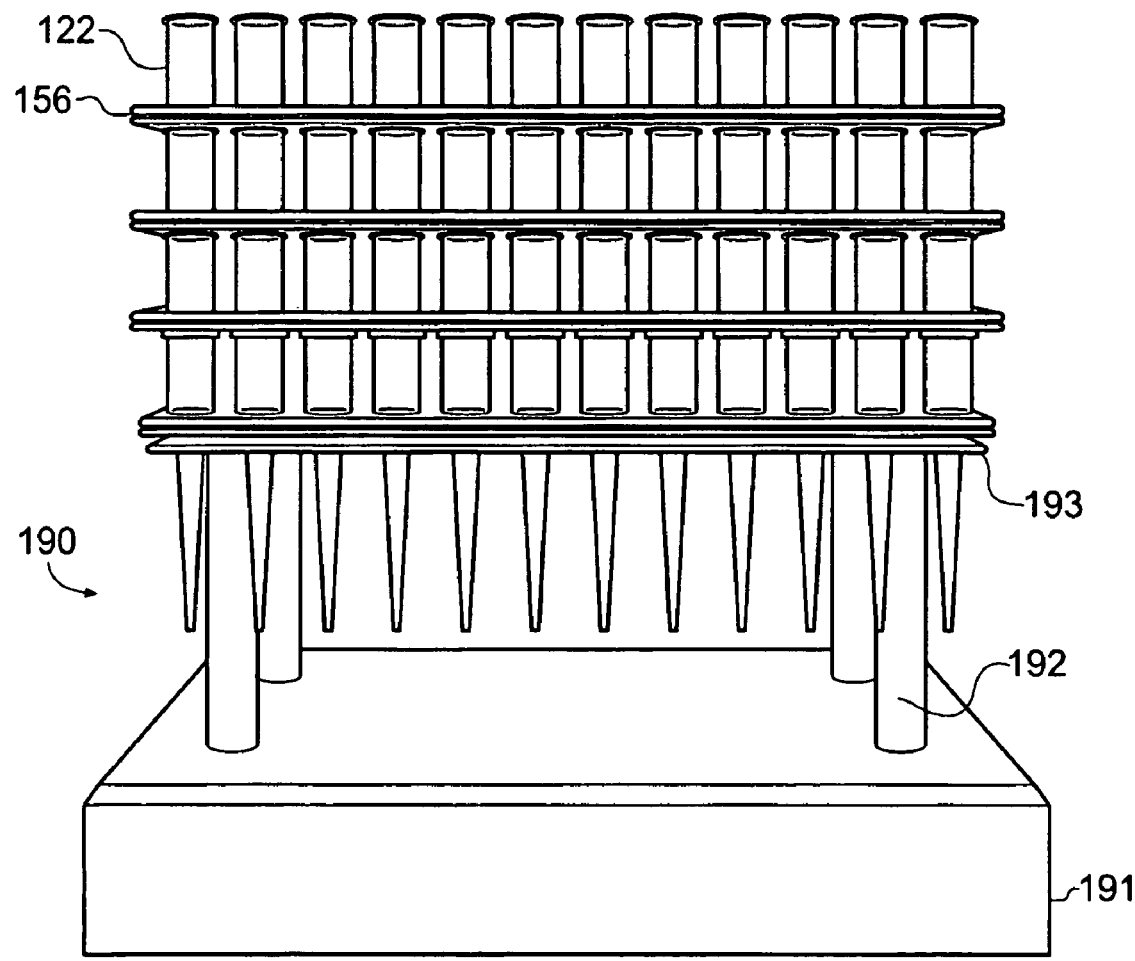
FIG. 16 is a side view of a storage cassette loading bay.

FIG. 16 is a side view of a storage cassette loading bay. The loading bay has a solid metal base 190 sufficiently heavy to provide stability on which four legs 192 stand in a rectangular arrangement. The legs 192 support a top 193 perforated with holes that match the holes in the pipette tip trays for which the loading bay is intended. A stack of pipette tip trays 156 with pipette tips 122 can be arranged on the top 193, a stack of four being shown in the figure. A stack of pipette tip trays can be conveniently inserted into an empty storage cassette by lifting the storage cassette over the loading bay, for example using its handle, and then lowering the storage cassette down onto the loading bay so that the trays push past the spring catches and into the storage shaft. The loading bay legs 192 have a length suitable for the loading, so that when the bottom of the storage cassette rests on the base 190, the plane of the loading bay top 193 is slightly above the plane of the horizontally extending part of the spring catches on which the lowest tray would normally bear.

Automated Head Changing

Figure 17:
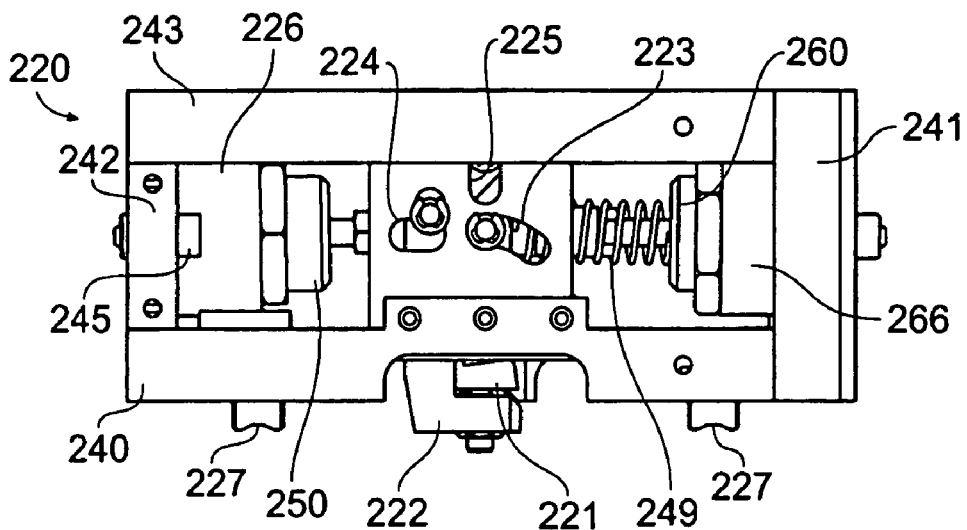
FIG. 17 is a side view of the head latching unit that is attached to the z-positioner motor drive.

FIG. 17 is a side view of the head latching unit 220 that is attached to the z-positioner motor drive and serves to allow different heads to be loaded and unloaded.

FIG. 18 is an exploded perspective view of the head latching mechanism of the head latching unit 220.

FIG. 19 is an exploded perspective view of the head latching unit 220 with the head latching mechanism of FIG. 18 partly assembled.

The head latching unit 220 comprises a housing made of top and bottom plates 243 and 240 and left and right end plates 242 and 241. Non-structural side plates 244 are also provided (omitted from FIG. 17, but evident in FIG. 19). The bottom plate 240 is provided on its lower side with locating stubs 227 to assist location of the head latching unit in corresponding holes in the heads.

The latching mechanism is driven by a push-me-pull-you pneumatic piston assembly comprising a delatch driving piston 250 and a latch driving piston 260 with respective cylinders 226 and 266. The cylinders 226 and 266 are rotatably mounted by spigots 252 (see FIG. 18) located in blocks 245 (see FIG. 19) secured to the base plate 240 in a manner similar to a howitzer.

The cylinders act on a knee joint 255 connecting to a floating upper joint 257 by an upper link 247. The knee joint 255 is also connected to a lower fixed joint 256 by a lower link 248. The fixed joint 256 is located in the side plates 246 (only one of which is shown in FIG. 18) by a locating pin. The knee joint 255 is connected to both pistons 250, 260 by respective connectors 251 assisted by a locating pin 253. The knee joint 255 has a pin 253 running through it which fits into a pair of arcuate slots 223 in the side plates 246 retained by a pair of outside circlips 254. The floating upper joint 257 also has a pin 253 running through it which fits in a pair of vertical slots 225 in the side plates 246 retained by a pair of outside circlips 254. The floating upper joint pin also pivotally mounts a latching arm 222. The latching arm 222 extends obliquely down to a non-jointed bend 258 with a hole through which a further pin 253 passes which is retained by outside circlips 254 and fits into an L-shaped slot 224 in the side plates 246. After the non-jointed bend 258, the latching arm 22 extends vertically down and then at right angles thereto extends further to form a latch support which bears a latch 221.

Before describing the latching action by which heads are attached to and detached from the latching unit 220, the latching parts of the heads are first described.

Figure 20:
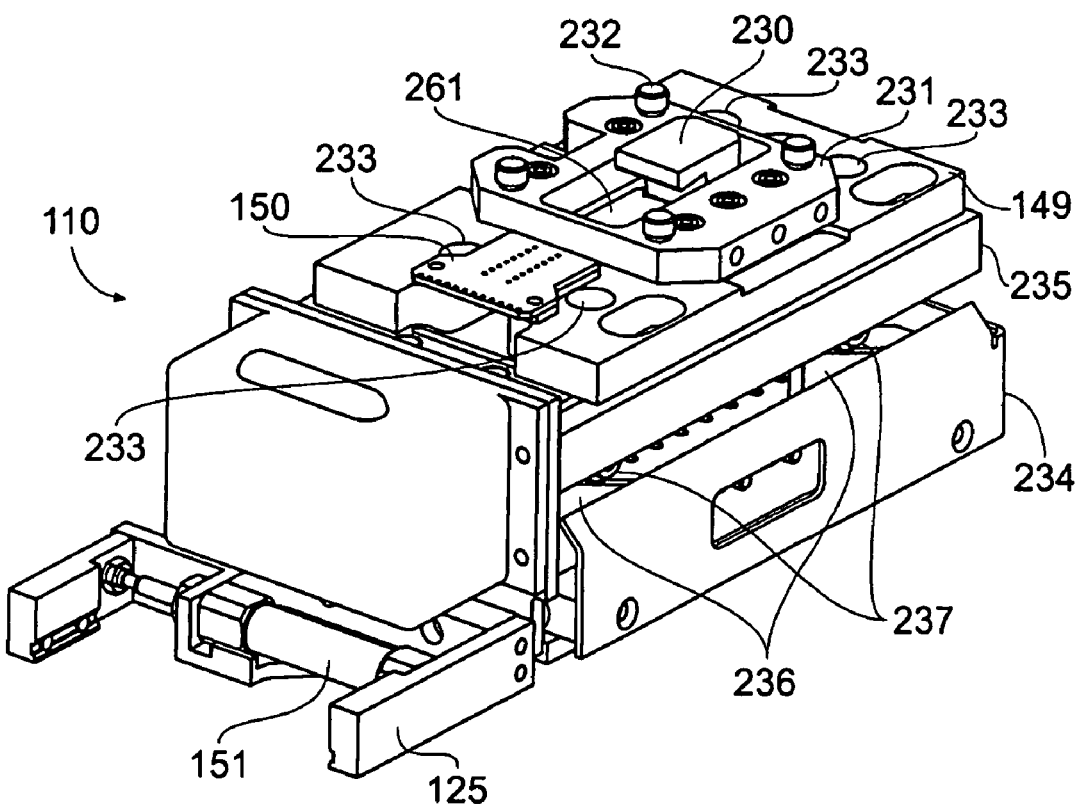
FIG. 20 is a perspective view of a liquid handling head showing parts used to secure the head to the head securing unit.

FIG. 20 is a perspective view of a liquid handling head 110 showing parts used to secure the head to the head securing unit. For completeness, it is noted that the liquid handling head illustrated is one for pipetting volumes of 1-50 microliters per pipette, in contrast to the larger volume pipetting provided by the liquid handling head illustrated in FIGS. 6 and 8. The latching components of all heads will be similar.

Parts familiar from the description of FIGS. 6 and 8 will be recognized, and not further described. These are the tray pincers 125, pincer motor drive 151, securing plate 149 and contact pad 150. Locating holes 233 for accepting the locating stubs 227 on the head latching unit 220 can be seen. In addition there are four locating stubs 232 on the head 110 which locate in corresponding holes in the head latching unit 220 (not visible in FIGS. 17-19). The stubs 232 are mounted on a plate 231 which mounts a lower latch 230 which has a fixed position and is shaped and dimensioned to engage with the latch 221 of the head latching unit.

Although not relevant for the latching, it is noted that FIG. 20 also shows upper and lower subassemblies 235 and 234 respectively. The lower subassembly 234 has ramps 236 on its upper surface on which ride wheels 237 that are carried by the upper subassembly 235. Riding up and down the ramps changes the separation between the subassemblies 235 and 234 and is the movement that provides the syringing action, the reservoir pistons being carried by the upper subassembly 235 and the reservoir cylinders being part of the lower subassembly 234. The motion is driven by an electric motor carried in the head.

Returning to the latching mechanism, this has two basic positions, a latched position, in which the head is gripped by the latch and securely engaged with the head latching unit 220, and a delatched pre-engagement position. FIGS. 17-19 illustrate the mechanism in the latched position. In view of this, movement of the mechanism from the latched position to the delatched position is described. This is the movement that would be performed when a head had been returned to its parking bay and was to be released by the head latching unit to allow the z-positioner with head latching unit to be moved away to pick up a different head.

Referring to FIG. 17, the delatching piston 250 is pneumatically actuated by compressed air through a feed line (not shown) which pushes the knee joint 255 to the right (as viewed in the figures) which pushes the pin around the arcuate slot 223. This forces the floating upper joint 257 vertically down guided and constrained by the vertical slot 225. Initially, the non-jointed bend 258 is also forced vertically down guided by the upright part of the L-shaped slot 224. During this phase of the delatching, the latch 221 is being moved vertically down, allowing it to become free of the head's latch 230 (assuming the head 110 is supported in its parking bay). Once the downward motion proceeds to the point at which the base of the L-shaped slot has been reached by the non-jointed bend 258 of the latching arm 222, the latching arm 222 is forced to rotate by the pin through the non-jointed bend 258 being confined to move in the base of the L-shaped slot until it abuts the end of the base section of the L-shaped slot. The mechanism is now in the delatched position, with the knee joint 255 at its maximum bend and the latching arm 222 at is maximum swing angle away from vertical, swung into a space 261 provided within the plate 231. At this point, the latching arm 222 has swung away sufficiently to allow the latching unit 220 to be lifted away from the head 110 by a simple vertical motion of the z-positioner. It will now be appreciated why the piston assemblies are pivotally mounted, namely to accommodate movement of the pins in the slots 223, 224 and 225.

Motion from the delatched to the latched position proceeds approximately in the reverse sequence. It is initiated by actuation of the latching piston 260 which acts on the knee joint 255 to straighten it out. The reverse sequence of slot motion is performed in relation to the latch-to-delatch motion with the latching arm 222 being forced to move vertically upward in the L-shaped slot 224 when the pin through the non-jointed bend 258 reaches the corner of the L-shaped slot 224. Worthy of mention is the fact that it in the final stages of straightening when moving into the latched position, the design allows a high amount of clamping force to be exerted, with the head's latch 230 being squeezed between the latching unit's latch 221 and the bottom of the lower link 248. This feature provides a highly secure latching of the head.

Figure 21:
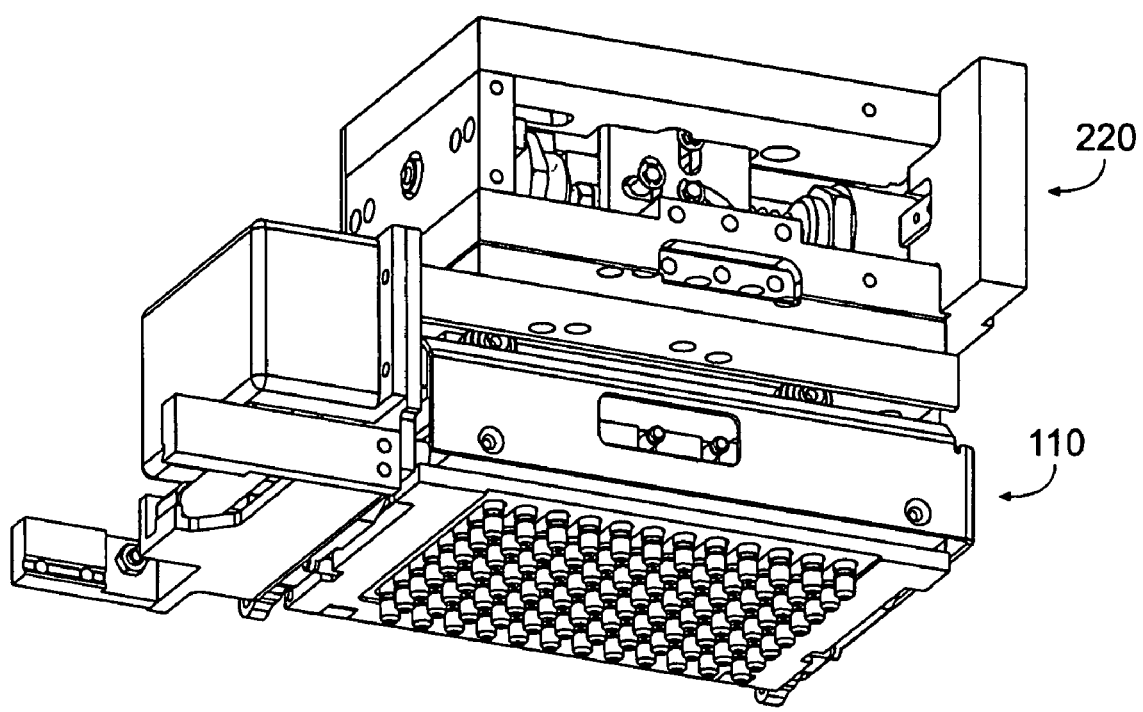
FIG. 21 shows the head attached to the head securing unit.

FIG. 21 shows the low volume liquid handling head 110 attached to the head securing unit 220 with the latching mechanism in the latched position described above.

It will be appreciated that although the automated head attachment and detachment has been described in relation to a liquid handling head, it is universally applicable to any head, for example pin heads for gridding or colony picking, thereby allowing multiple functions to be performed by a single robot.

What is claimed is:

1. A robot for handling biological sample containers, comprising:
    (a) a head for carrying out processes on biological sample containers;
    (b) a positioning apparatus for moving the head around the robot;
    (c) an attachment mechanism; and
    (d) a parking station for parking the head,
    wherein the head: (i) is connected to the positioning apparatus by the attachment mechanism which is drivable between a clamped state, in which the head is secured to the positioning apparatus, and a released state, in which the head can be detached from the positioning apparatus and deposited in the park station, and (ii) is configured with resident logic comprising head identification data;
    wherein the attachment mechanism includes a communication feed-through to transmit the head identification data from the head to a computer control system, and wherein the communication feed-through comprises an electrical contact pad on the head which is connected to a corresponding contact pad on the attachment mechanism to allow transmission of identification data from the resident logic located in the head to the computer control system; and,
    wherein the parking station functions to house the head when the head is not attached to the positioning apparatus.

2. The robot according to claim 1, wherein the park station comprises a plurality of parking bays, each for parking one head.

3. The robot according to claim 2, comprising a further head.

4. The robot according to claim 3, wherein the head and the further head are both liquid handling heads for pipetting.

5. The robot according to claim 3, wherein the head is a liquid handling head and the further head is a pin head for pipetting, colony picking, spotting, gridding or any combination thereof.

6. The robot according to claim 3, wherein the head and the further head 30 are both pin heads for pipetting, colony picking, spotting, gridding or any combination thereof.

7. The robot according to claim 1, wherein the attachment mechanism comprises a piston assembly arranged to actuate a knee joint connected to a latch, the knee joint adopting a bent position in the released state mid straightened position in the clamped state.

8. The robot according to claim 7, wherein the piston assembly includes two piston cylinder units arranged in a push-me-pull-you configuration either side of the knee joint.

9. The robot according to claim 1, wherein the contact pad further provides the head with electrical power feeds.

10. A releasable head for a biological sample container handling robot, comprising:
    (a) a communication feed-through for communicating to a robot to which the head is attached, wherein the communication feed-through comprises an electrical contact pad which connects the head to the robot allowing transfer of head-identification data from the head to a computer control system; and
    (a) a resident logic component located in the head which allows communication of the head identification data to the computer control system through the communication feed-through to identify the head attached to the robot.

11. The head according to claim 10, wherein the contact pad further provides the head with electrical power feeds.

12. The head according to claim 10, wherein the head is a liquid handling head for pipetting.

13. The head according to claim 10, wherein the head is a pin head for pipetting, colony picking, spotting, gridding or any combination thereof.

* * * * *